United States Patent [19]
Yasui

[11] Patent Number: 5,932,273
[45] Date of Patent: Aug. 3, 1999

[54] GUMI CANDIES AND A PROCESS FOR MAKING THE SAME

[75] Inventor: Hiroyuki Yasui, Nagoya, Japan

[73] Assignees: Mondo Beni Co., Ltd., Hyogo; Yasui Confectionery Co. Ltd., Aichi, both of Japan

[21] Appl. No.: 08/817,994

[22] PCT Filed: Sep. 5, 1996

[86] PCT No.: PCT/JP96/02513

§ 371 Date: Apr. 30, 1997

§ 102(e) Date: Apr. 30, 1997

[87] PCT Pub. No.: WO97/08962

PCT Pub. Date: Mar. 13, 1997

[30] Foreign Application Priority Data

Sep. 5, 1995 [JP] Japan ................................. 7-228209

[51] Int. Cl.6 ....................... A23L 1/0524; A23L 1/0562; A23G 3/00
[52] U.S. Cl. ..................... 426/576; 426/577; 426/578; 426/660
[58] Field of Search ..................... 426/576, 577, 426/578, 660

[56] References Cited

U.S. PATENT DOCUMENTS

| | | | |
|---|---|---|---|
| 1,552,428 | 1/1925 | Ferguson | 426/576 |
| 4,082,857 | 4/1978 | Croome | 426/576 |
| 4,292,337 | 9/1981 | Andersen | 426/576 |
| 4,597,981 | 7/1986 | Kastin | 426/576 |
| 5,328,711 | 7/1994 | Coleman | 426/576 |
| 5,549,921 | 8/1996 | Robinson et al. | 426/576 |

FOREIGN PATENT DOCUMENTS

| | | |
|---|---|---|
| 61-87562 | 5/1986 | Japan . |
| 64-30548 | 2/1989 | Japan . |
| 3-61457 | 9/1991 | Japan . |
| 05068481 | 3/1993 | Japan . |
| 06070704 | 3/1994 | Japan . |
| 8-116891 | 5/1996 | Japan . |

*Primary Examiner*—Helen Pratt
*Attorney, Agent, or Firm*—Armstrong, Westerman, Hattori, McLeland & Naughton

[57] ABSTRACT

"Gumi" (or gummy) candies made by mixing water, sugar, starch syrup, an acid, a setting agent, a buffer solution, a flavoring material and a coloring agent. A combination of pectin and gelatin is used as the setting agent. Pectin and gelatin are used in the amounts of 1.9 to 2.6% and 1 to 3.8%, respectively, by weight relative to the total solid weight of the principal materials which are sugar, starch syrup, acid, setting agent and a buffer solution.

4 Claims, No Drawings

GUMI CANDIES AND A PROCESS FOR MAKING THE SAME

TECHNICAL FIELD

This invention relates to "gumi" (or gummi, or gummy) candies, which are jelly-like candies, and a process for making the same. More particularly, it relates to gumi candies retaining good consistency even at, say, 80° C. and a process for making the same.

BACKGROUND ART

The conventional gumi candies have been made by mixing water, sugar, starch syrup, citric or other acid assisting setting, a setting agent, a buffer solution of e.g. sodium citrate or acetate for preventing too rapid solidification of a solution of materials as poured into a mold, a flavoring material giving the flavor of e.g. apples or peppermint, and a coloring agent. Gelatin has been used as the setting agent in the amount of, say, 3 to 19% by weight relative to the total weight of the materials including water and the flavoring material (see Japanese Patent Application laid open under No. Hei 6-70704).

The conventional gumi candies have, however, melted at, say, 40–45° C., and been unable to retain their shape. It has, therefore, been impossible to sell them by an automatic vending machine exposed to an ambient temperature of, say, 80° C. under the blazing sun in midsummer.

Besides gelatin, agar and pectin are known as a setting agent used in ordinary jellies, and it may be possible to use agar or pectin as a setting agent for gumi candies.

If agar is used instead of gelatin, however, there have been cases in which setting is prevented by citric or other acid used for assisting setting.

If pectin is used instead of gelatin, it is possible to make gumi candies having satisfactory heat resistance. They cannot, however, be called gumi candies any longer, since they lose their characteristic elastic resistance to biting off with the teeth, though they may be somewhat tough and elastic to the touch.

Japanese Patent Application laid open under No. Hei 5-68481 discloses gumi candies made by using both gelatin and pectin, but the pectin in those candies is used not for improving their heat resistance, but merely for making a change of materials so that two kinds of gumi candies may not melt with each other during casting by a double depositor. Those candies contain only a small amount of pectin not exceeding one-twentieth of that of gelatin, and melt at, say, 45° C.

It is an object of this invention to solve the problems as pointed out above, and provide gumi candies which retain good consistency even at a high temperature without having any undesirable lowering in elastic resistance to the teeth.

It is another object of this invention to provide a method which can make gumi candies having good consistency even at a high temperature, a good elastic resistance to the teeth and a good appearance, while containing an extract of persimmons as an oral deodorant.

DISCLOSURE OF THE INVENTION

The gumi candies according to this invention are the gumi candies made by mixing water, sugar, starch syrup, an acid, a setting agent, a buffer solution, a flavoring material and a coloring agent, and characterized in that a combination of pectin and gelatin is used as the setting agent, and that the pectin and gelatin are used in the amounts of 1.9 to 2.6% and 1 to 3.8%, respectively, by weight relative to the total solid weight of the principal materials consisting of the sugar, starch syrup, acid, setting agent and buffer solution.

The gumi candies may further contain an oral deodorant. An extract of persimmons having a high deodorizing power is a preferred oral deodorant.

The gumi candies according to this invention have good consistency even at, say, 80° C., while retaining their characteristic resistance to biting off with the teeth, since they contain as the setting agent a combination of pectin and gelatin in the amounts of 1.9 to 2.6% and 1 to 3.8%, respectively, by weight relative to the total solid weight of the principal materials consisting of the sugar, starch syrup, acid, setting agent and buffer solution.

If the amount of pectin is less than 1.9% by weight, the candies have a lower resistance to heat, and if it exceeds 2.6% by weight, they become too tough to remain elastic and be called gumi candies.

If the amount of gelatin is less than 1% by weight, the candies become too tough to remain elastic, and if it exceeds 3.8% by weight, they become too soft, as they need a large amount of water, and in either event, they lose the resistance to the teeth which is characteristic of the gumi candies.

If they contain an oral deodorant, the gumi candies exhibit an oral deodorizing action when held in the mouth.

A particularly high deodorizing effect can be obtained if an extract of persimmons is used as the oral deodorant.

As an extract of persimmons, it is possible to use, for example, a juice as extracted from unripe fruits of persimmons, such as "fuyugaki", "hirakakunashigaki", "hachiyatanegaki" or astrigent persimmons (it is possible to press 5 kg of juice from 10 kg of unripe persimmons), or a sugarless juice obtained by removing sugar from the extracted juice, or a powder obtained by removing water from any such juice, as shown in Japanese Patent Publication No. Hei 3-61457.

In the event that an extract of persimmons is used as the oral deodorant, it is possible to make gumi candies having a good elastic resistance to the teeth and a good appearance despite the presence of the extract of persimmons if they are made by preparing a solution of a mixture of water, a part of acid, a buffer solution, sugar, starch syrup and pectin, adding the extract into the solution under stirring, and dissolving, then, the rest of the acid, a coloring agent, a flavoring material and gelatin therein.

If the extract of persimmons, as well as the coloring agent and the flavoring material, is added into the solution of a mixture of water, acid, buffer solution, sugar and starch syrup after both pectin and gelatin are added as the setting agent, as in the case of an ordinary method of making gumi candies, a large amount of a fibrous substance (which is considered as a reaction product of tannin and other constituents of the extract of persimmons and the protein in the gelatin) is produced in the solution, and lowers the elastic resistance of gumi candies to the teeth and their appearance, though they may retain consistency at, say, 80° C.

According to the method of this invention for making gumi candies, however, the extract of persimmons is added under stirring into the solution of a mixture of water, a part of acid, buffer solution, sugar, starch syrup and pectin, so that tannin and other constituents of the extract may be dispersed and diluted before gelatin is added, so that the subsequent addition of the protein forming the gelatin may not result in the formation of any fibrous substance lowering the elastic resistance of gumi candies to the teeth and their appearance.

BEST MODE OF CARRYING OUT THE INVENTION

Table 1 below shows the raw materials used for making gumi candies embodying this invention.

TABLE 1

| Order of addision | | Weight (kg) | Solid weight of principal materials (kg) | Solid weight ratio of principal materials (wt %) |
|---|---|---|---|---|
| A | Water | 25 | | |
|   | Sodium citrate | 0.35 | 0.35 | 0.5 |
|   | Citric acid (a 50% by weight aqueous solution) | 0.75 | 0.375 | 0.5 |
| B | Pectin | 1.8 | 1.8 | 2.3 |
|   | Sugar | 5.5 | 5.5 | 7.1 |
| C | Sugar (containing 17% sorbitol) | 46 | 46 | 59.4 |
|   | Starch syrup (containing oligosaccharide, and having a Brix degree of 73) | 30 | 21.9 | 28.3 |
| D | Oral deodorant (extract juice of persimmons) | 5 | | |
| E | Citric acid (a 50% by weight aqueous solution) | 0.9 | 0.45 | 0.6 |
|   | Gelatin (a 40% by weight aqueous solution) | 2.5 | 1 | 1.3 |
|   | Coloring agent: | | | |
|   | Yellow pigment | 0.03 | | |
|   | Blue pigment | | | |
|   | Flavoring material: | | | |
|   | Apple | 0.215 | | |
|   | Peppermint | 0.095 | | |
| Total weight | | 118.14 | 77.375 | |
| Volatie loss | | 33.14 | | |
| Yield | | 85 | | |

The steps 1 to 7 as described below are taken for making gumi candies from the materials as shown above.

1. Water, A in Table 1, is put in a melting pot, and citric acid and sodium citrate, A, are added, and dissolved in it.
2. Pectin and sugar, B, are mixed in powder form, and their mixture is put in the melting pot, so that pectin, B, may not form any mass. AS Confectionery made by GENU, which sets slowly, is used as pectin, so that a casting time of, say, 30 minutes at, say, 60° C. may be ensured during the later step of casting the mixture into a mold.
3. The solution in the melting pot is slowly heated under stirring until it boils, and after it has boiled, its heating is continued for one or two more minutes, so that the pectin (AS Confectionery) may be thoroughly dissolved.
4. Sugar, C, is added and dissolved in the solution under boiling, so that the solution may not be unduly cooled, and starch syrup is, then, added.
5. If the solution is heated to, say, 107° C., an extract of persimmons (more specifically, a juice extracted from 10 kg of fruits by a press) is added as an oral deodorant, D, under stirring, and the solution is further heated to, say, 110° C.
6. Admixed successively under stirring are an aqueous solution of citric acid, E, and an aqueous solution of gelatin, E (as obtained by dissolving 1 kg of gelatin in 1.5 kg of water), a yellow safflower pigment and a blue gardenia pigment as coloring agents, and flavoring materials giving the flavors of apples and peppermint.
7. Upon cooling to, say, 90° C., the solution is cast into a starch mold, and dried in a drying chamber for 12 hours, while it is held at 60° C. Then, 36 hours of cooling at ordinary temperature, oil and wafer coating, and wrapping yield gumi candies.

The gumi candies preferably have a Brix degree of 81 to 86 so as to remain in good condition for a long time (the candies made from the materials shown in Table 1 had a Brix degree of 82.5). The gumi candies having a Brix degree of less than 81 are likely to get moldy and are too soft, while those having a Brix degree over 86 are too hard, and in either event, their elastic resistance to the teeth is too low for any satisfactory gumi candies.

It is also desirable from the standpoint of their setting time that the gumi candies have a pH of 3.5 to 3.8 (the candies made from the materials shown in Table 1 had a pH of 3.55). A mixture of materials giving gumi candies having a pH below 3.5 sets too rapidly for proper casting, while one giving candies having a pH above 3.8 fails to set.

The gumi candies made as described retain an elastic resistance to biting off with the teeth, as is characteristic of these kind of candies, and consistency at, say, 80° C. (the candies embodying this invention began to soften at about 80° C. and melted at about 100° C.).

The gumi candies exhibit an oral deodorizing action when held in the mouth, since they contain an extract of persimmons as the oral deodorant.

The addition of an extract of persimmons as the oral deodorant does, of course, not have any adverse effect on the elastic resistance or appearance of the gumi candies, since the extract of persimmons is mixed in the solution obtained by mixing water, a part of acid, buffer solution, sugar, starch syrup and pectin, so that tannin and other constituents thereof may be dispersed and diluted in the solution before gelatin is added, so that the later addition of the protein from gelatin may not result in the formation of any fibrous substance.

Although the juice as pressed has been used as the extract of persimmons in the gumi candies embodying this invention, it is alternatively possible to use a sugarless juice obtained by removing sugar from the juice as pressed, or a powder obtained by removing water from the juice, or sugarless juice. In the event that a powder is used, it is dissolved in water, and used as an aqueous solution having a concentration of, say, 10% by weight.

It is possible to use flavonoid, or an extract of tea leaves as the oral deodorant, though they are inferior to an extract of persimmons as a deodorant.

As a result of the attempts to make candies by employing different amounts of pectin and gelatin, it has been found that the adequate amount of pectin is from 1.9 to 2.6% by weight relative to the total solid weight of the principal materials consisting of sugar, starch syrup, acid, setting agent and buffer solution. If its amount is less than 1.9% by weight, the candies have a lower resistance to heat, and if it exceeds 2.6% by weight, they become too tough to remain elastic and be called gumi candies.

It has also been found that the adequate amount of gelatin is from 1 to 3.8% by weight relative to the total solid weight of the principal materials consisting of sugar, starch syrup, acid, setting agent and buffer solution. If its amount is less than 1% by weight, the candies become too tough to remain elastic, and if it exceeds 3.8% by weight, they become too soft, as they need a large amount of water, and in either event, they lose the elastic resistance to the teeth which is characteristic of the gumi candies.

The use of the slowly setting AS Confectionery made by GENU as pectin to ensure a casting time of, say, 30 minutes at, say, 60° C. enables casting into a starch mold to be continued without being interrupted by any undesirably rapid setting, so that the gumi candies can be made on a mass-production basis.

Although citric acid has been used as the acid for assisting the setting of the gumi candies embodying this invention, it is also possible to use another organic acid, such as malic acid, tartaric acid, fumaric acid, adipic acid, lactic acid, acetic acid, or vinegar. The acid is added in in such an amount that the solution of the materials may not set before its complete casting, but may not fail to set thereafter to make gumi candies having a pH of 3.5 to 3.8. A solution giving candies having a pH below 3.5 sets too rapidly for proper casting, while a solution giving candies having a pH above 3.8 fails to set, as already stated.

Although sodium citrate has been used as the buffer solution for the candies embodying this invention, it is also possible to use, for example, sodium acetate.

INDUSTRIAL UTILITY

The gumi candies of this invention are of utility, since they retain consistency even in an atmosphere having a temperature of, say, 80° C., as stated above.

What is claimed is:

1. Gumi candies made by mixing water, sugar, starch syrup, an acid, a setting agent, a buffer solution, a flavoring material and a coloring agent, and characterized in that a combination of pectin and gelatin is used as said setting agent, and that said pectin and gelatin are used in the amounts of 1.9 to 2.6% and 1 to 3.8%, respectively, by weight relative to the total solid weight of the principal materials consisting of said sugar, starch syrup, acid, setting agent and buffer solution, such that the gumi candies produced have good consistency at a temperature of about 80° C.

2. Gumi Candies as set forth in claim 1, further containing an oral deodorant.

3. Gumi Candies as set forth in claim 2, wherein said oral deodorant is an extract of persimmons.

4. A process for making gumi candies made by mixing water, sugar, starch syrup, an acid, pectin and gelatin as a setting agent, a buffer solution, a flavoring material, a coloring agent, and an extract of persimmons as an oral deodorant, while using said pectin and gelatin in the amounts of 1.9 to 2.6% and 1 to 3.8%, respectively, by weight relative to the total solid weight of the principal materials consisting of said sugar, starch syrup, acid, setting agent and buffer solution, said process comprising preparing a solution of a mixture of said water, a part of said acid, and said buffer solution, sugar, starch syrup and pectin, mixing said extract in said solution under stirring, and dissolving the rest of said acid, and said coloring agent, flavoring material and gelatin in said solution.

* * * * *